(12) United States Patent
Evans et al.

(10) Patent No.: US 7,704,932 B2
(45) Date of Patent: Apr. 27, 2010

(54) PERSONAL CLEANING COMPOSITIONS

(75) Inventors: Erica Louise Evans, Marlborough (GB);
Marc Paul Lorenzi, Egham (GB);
Nicola Jacqueline Phipps, Bracknell (GB)

(73) Assignee: The Procter & Gamble Company, Cincinnati, OH (US)

( * ) Notice: Subject to any disclaimer, the term of this patent is extended or adjusted under 35 U.S.C. 154(b) by 658 days.

(21) Appl. No.: 10/981,049

(22) Filed: Mar. 14, 2005

(65) Prior Publication Data

US 2005/0153852 A1    Jul. 14, 2005

(51) Int. Cl.
*C11D 1/94* (2006.01)
(52) U.S. Cl. ....................................................... 510/101
(58) Field of Classification Search .................. 510/101
See application file for complete search history.

(56) References Cited

U.S. PATENT DOCUMENTS

| | | | | |
|---|---|---|---|---|
| 5,236,710 | A | * | 8/1993 | Guerrero et al. ............ 424/401 |
| 5,336,497 | A | * | 8/1994 | Guerrero et al. ............ 424/401 |
| 5,520,839 | A | | 5/1996 | Hall et al. |
| 5,780,404 | A | | 7/1998 | Bacon et al. |
| 5,833,999 | A | | 11/1998 | Trinh et al. |
| 5,942,217 | A | | 8/1999 | Woo et al. |
| 6,113,892 | A | * | 9/2000 | Newell et al. ............ 424/70.19 |
| 6,204,229 | B1 | | 3/2001 | Hasegawa et al. |
| 6,346,260 | B1 | * | 2/2002 | Holzl et al. ................. 424/404 |
| 6,379,681 | B1 | | 4/2002 | Bordat et al. |
| 6,730,655 | B2 | * | 5/2004 | Reinehr et al. ............... 510/504 |
| 2002/0055452 | A1 | | 5/2002 | McGee et al. |
| 2003/0087776 | A1 | | 5/2003 | Heltovics et al. |
| 2003/0134759 | A1 | | 7/2003 | Geary et al. |
| 2003/0166497 | A1 | | 9/2003 | Yang |
| 2003/0166498 | A1 | | 9/2003 | Yang |
| 2003/0166499 | A1 | | 9/2003 | Yang |
| 2003/0219392 | A1 | * | 11/2003 | Kung et al. .................... 424/59 |
| 2004/0091628 | A1 | | 5/2004 | Heltovics et al. |

FOREIGN PATENT DOCUMENTS

| | | |
|---|---|---|
| EP | 0 554 024 B1 | 7/1997 |
| WO | WO 97/48374 A2 | 12/1997 |
| WO | WO 97/48375 A2 | 12/1997 |
| WO | WO 97/48378 A1 | 12/1997 |
| WO | WO 02/34225 A1 | 5/2002 |
| WO | WO 02/098966 A1 | 12/2002 |
| WO | WO 03/015736 A2 | 2/2003 |

OTHER PUBLICATIONS

The Chemistry of Essential Oils and Artifical Perfumes, vol. 1, Ernest J. Parry, 4th ed., 1921, Scott, Greenwood and Son, pp. 395-400, 418, 419, 425-427.*
Lawrence, Dr. B. M., "Progress in Essential Oils", Perfume and Flavourist, vol. 24, No. 1, pp. 53-63 (Jan./Feb. 1999), (ISSN: 1041-2905).

\* cited by examiner

*Primary Examiner*—John R Hardee
(74) *Attorney, Agent, or Firm*—Mark A. Charles

(57) ABSTRACT

Personal cleansing compositions, especially body washes and shampoos, are disclosed comprising surfactant, fragrance oil and less than about 7.5% non-fragrance oil, wherein the surfactant and fragrance oil form:
  a) a first micellar phase; and
  b) a second phase which rotates polarized light.

21 Claims, 1 Drawing Sheet

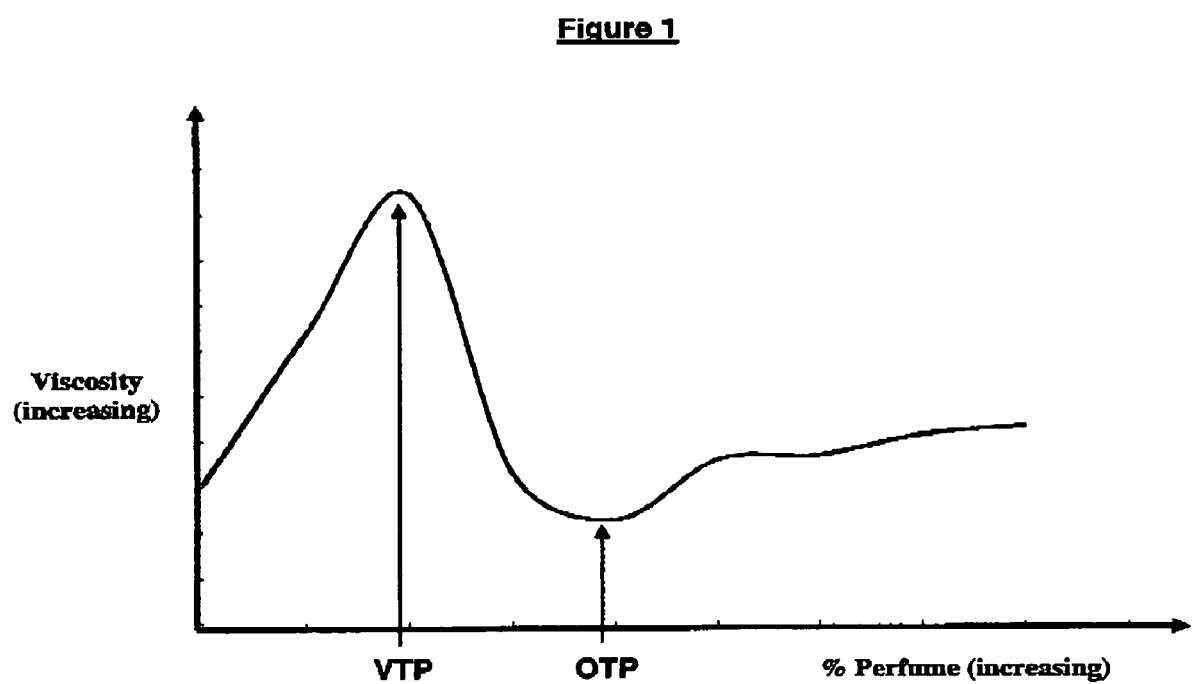

PERSONAL CLEANING COMPOSITIONS

CROSS REFERENCE TO RELATED APPLICATION

This application claims the benefit of U.S. Application No. 60/517,025, filed Nov. 4, 2003.

FIELD OF THE INVENTION

The present application relates to the field of personal cleansing, such as liquid soaps, body washes and shampoos.

BACKGROUND OF THE INVENTION

Soap-like material found in clay cylinders during the excavation of ancient Babylon is evidence that soap making was known as early as 2800 B.C. Inscriptions on the cylinders teach us that the contents had been made by boiling fats with ashes—a method of making soap. Later on, particularly in the $19^{th}$ Century, it became common to add fragrances to soap to mask the natural smell of some of the fats used, particularly if these were animal fats, and for other aesthetic reasons.

The personal cleansing compositions used today may still include natural soaps, such as those described above, as well as synthetic soaps, which were developed during the First World War. Such cleansing compositions may take a number of forms including liquid soaps, soap bars, shampoos and body washes. The overwhelming majority of these compositions now comprise some kind of fragrance—indeed, nowadays, the fragrance is one of the key parameters driving consumer acceptance of these products.

A difficulty encountered with fragranced personal cleansing compositions is that the fragrance oils are solubilized within the surfactant micelles such that they either remain micellised or enter the continuous aqueous phase. Either way, the result is that they are typically rinsed away during the washing process rather than being deposited onto the skin as intended.

Previous researchers have employed a number of methods to counter this effect. One approach discussed in EP 0 554 024 has been to reduce solubilization of the perfume oil in the surfactant phase by adding an oil phase in which the perfume oils may reside. As a result of the oil's natural hydrophobicity, that oil phase, including the perfume oil, may deposit relatively well onto skin. A similar approach is discussed in WO 03/015736, which relates to the dissolution of the perfumes in a water-immiscible silicone phase. Again, the naturally hydrophobic silicone phase may lead to improved deposition of the fragrance oil onto skin. These approaches involve the inclusion of an additional material to the formulation to enhance fragrance delivery. That additional material may, however, have negative implications for the overall performance of the formulation, such as the lather profile.

An alternative approach discussed in WO 97/48374, WO 97/48375 and WO 97/48378, has been to form coacervates between anionic surfactant and cationic polymers, which coacervates are allegedly capable of entrapping the perfume, depositing on the skin and thus enhancing perfume deposition. The benefit of this approach is, however, limited by the nature of the surfactant and the cationic polymer, because only a few surfactant-polymer combinations will actually form coacervates, and the surfactants and polymers concerned may not be particularly suitable for personal cleansing applications (they do not necessarily give good lathering and are not necessarily mild enough).

A further alternative discussed in US 2003/166497, US 2003/166498 and US 2003/166499 has been to design the perfume/surfactant system such that, on dilution, micelles are designed to disappear due to their high Critical Micelle Concentration (CMC), and deliver fragrance bloom. After blooming from the micelles, the perfume materials enter the water continuous phase and may be washed away during rinsing. Once again, the surfactant phase is essentially a micellar phase. As discussed hereinbelow, it is believed that perfume does not deposit sufficiently well via a micellar phase.

It would be desirable to design fragranced personal cleansing products having improved perfume deposition on skin. Furthermore, it would be desirable to achieve that without adding new materials to the composition which might have negative implications for other aspects of the products' performance.

SUMMARY OF THE INVENTION

According to the present invention, a personal cleansing composition is provided comprising surfactant, fragrance oil and less than about 7.5% non-fragrance oil, wherein the surfactant and fragrance form:

a) a first micellar phase; and
b) a second phase which rotates polarized light.

According to a further aspect of the invention, a personal cleansing composition is provided comprising anionic surfactant, amphoteric surfactant, fragrance oil and less than about 7.5% wt non-fragrance oil, wherein the surfactant and fragrance oil form:

a) a first micellar phase; and
b) a second phase which rotates polarized light.

According to a further aspect of the invention, body a wash composition is provided comprising anionic surfactant and amphoteric surfactant in the ratio of anionic to amphoteric surfactant from about 6:1 to about 1:3, from about 2% wt to about 4% wt fragrance oil and less than about 7.5% wt non-fragrance oil, wherein the surfactant and fragrance oil form:

a) a first micellar phase; and
b) a second phase which rotates polarized light.

According to a further aspect of the invention, a personal cleansing composition is provided comprising surfactant, fragrance oil, less than about 7.5% non-fragrance oil, and a stabiliser wherein the surfactant and fragrance oil form:

a) a first micellar phase; and
b) a second phase which rotates polarized light.

These and other features, aspects, and advantages of the present invention will become evident to those skilled in the art from a reading of the present disclosure.

BRIEF DESCRIPTION OF THE DRAWINGS

FIG. 1 is a typical graph of increasing perfume concentration versus increasing personal cleansing composition viscosity, illustrating the viscosity transition point (VTP) and opacity transition point (OTP), as discussed and defined hereinbelow.

DETAILED DESCRIPTION OF THE INVENTION

While the specification concludes with claims which particularly point out and distinctly claim the invention, it is believed the present invention will be better understood from the following description of preferred embodiments taken in conjunction with the accompanying drawing.

All weights, measurements and concentrations herein are measured at 25° C. on the composition in its entirety, unless otherwise specified.

Unless otherwise indicated, all percentages of compositions referred to herein are weight percentages of the total composition (i.e. the sum of all components present) and all ratios are weight ratios. In addition, unless stated otherwise, weight percentages and ratios refer in all cases to the weight percentage or ratio of fragrance material.

Unless otherwise indicated, all polymer molecular weights are weight average molecular weights.

Unless otherwise indicated, the content of all literature sources referred to within this text are incorporated herein in full by reference.

Except where specific examples of actual measured values are presented, numerical values referred to herein should be considered to be qualified by the word "about".

As discussed above, others have tried to address the problem of enhancing fragrance deposition from rinse off personal cleansing products by adding oils, silicones and polymers to their compositions. The present inventors have unexpectedly found that the deposition of perfume onto skin can be enhanced just by manipulating surfactant phase behavior. More unexpectedly still, it has been found that the mere addition of fragrance to the surfactant matrix may trigger those phase changes. The present inventors have established that addition of fragrance to a surfactant matrix results in a series of phase changes, which phase changes may be observed as changes in viscosity, opacity changes and changes in the ability to rotate polarised light.

On addition of fragrance to a surfactant matrix, a viscosity increase is observed up to a maximum, which may be referred to as the Viscosity Transition Point (VTP)—this maximum can clearly be seen in FIG. 1. Above the VTP, further addition of fragrance results in phase changes, the precise nature of which is not completely understood. These phase changes result in a viscosity decrease, as can be seen from FIG. 1, and, at a specific point, which is dependent on the nature of the surfactant and fragrance employed, a disperse phase forms. If the surfactant matrix otherwise exhibits some transparency, then the matrix itself is observed to become opaque. The point at which this opacity change takes places may be referred to as the Opacity Transition Point (OTP) and is illustrated in FIG. 1. Typically, the OTP occurs in compositions having a fragrance level of between about 1% wt and about 4% wt, depending on the precise fragrances and surfactants present, and, as discussed hereinbelow, the precise fragrance concentration at which the OTP occurs may also be manipulated. Without wishing to be bound by theory it is believed that the dispersed phase formed comprises multi-lamellar vesicles and a lamellar phase (this phase shall be referred to hereafter as the "second phase"). Above the OTP fragrance deposition significantly increases. Again, without wishing to be bound by theory, it is believed that this improved deposition is causally linked to the formation of the second phase.

The present inventors have also established that, for any given system, the second phase may be formed at lower perfume levels by manipulating certain system parameters. With reference to FIG. 1, this manipulation has the effect of shifting the entire curve to the left—this means that the perfume concentration at which the VTP and OTP occur is decreased. Without wishing to be bound by theory, it is believed that these manipulations may enhance surfactant packing thereby decreasing the level of fragrance required to form the second phase. This effect may be achieved by making any changes that enhance surfactant packing. Non-limiting examples of such changes include the addition of materials that increase packing, such as fatty alcohols, fatty acids, alkoxylated fatty alcohols, alkoxylated fatty acids, salts and mixtures thereof; lowering the pH; altering the ratio of anionic: amphoteric surfactants; altering the ratio of anionic: cationic surfactants; combinations of all of these measures. Formation of the second phase at lower perfume levels may increase the fragrance delivery efficiency.

Once the product passes the OTP it contains at least two phases which are believed to be a first continuous micellar phase (hereafter referred to as the "first phase") and a discrete, second phase. The different phases exhibit a number of different functional behaviors, including different viscosities, turbidities, perfume content and ability to rotate polarized light, an ability also known as birefringence—some of these behaviors are discussed hereinbelow. The second phase has a much greater degree of opacity, has a higher viscosity, is more stable and is perfume enriched (by weight) with respect to the first micellar phase. In addition, it rotates polarized light, which the first micellar phase does not.

Without wishing to be bound by theory, it is believed that, in use, surfactants in the thinner first micellar phase contribute to the lather of the product and release the fragrance they contain to enhance the fragrance bloom. The more viscous second phase is more stable than the first micellar phase and is therefore slow to solubilize on dilution. This slow dissolution results in enhanced phase deposition, and hence enhanced fragrance deposition.

The personal cleansing compositions according to the invention may comprise from about 0.1 to about 30% wt surfactant, preferably from about 1% wt to about 27.5% wt, more preferably from about 3.0% wt to about 25% wt, even more preferably from about 5% wt to about 20% wt, more preferably still from about 11% wt to about 18% wt.

Surfactants which may be employed include anionic lathering surfactants, amphoteric lathering surfactants, non-ionic lathering surfactants, cationic surfactants and mixtures thereof. Examples of such surfactants may be found in McCutcheon's, Detergents and Emulsifiers, North American Edition (2001), published by Allured Publishing Corporation, which is hereby incorporated herein by reference. Cationic lathering surfactants are generally not to be used alone, but in combination with other lathering surfactants.

It is not essential that any particular type of surfactant be present for the invention to be carried out—the first and second phases according to the invention may be formed with any surfactant, bearing in mind the proviso in relation to cationic surfactants, above. It is, however, preferred that the personal cleansing compositions according to the invention comprise a mixture of anionic and amphoteric lathering surfactants. This combination gives an appropriate balance of lather volume, from the anionic surfactant, and mildness from the anionic and amphoteric surfactants.

Anionic lathering surfactants which may be employed according to the invention include alkyl sulfates, alkyl ether sulfates, sulfated monoglycerides, sulfonated olefins, alkyl aryl sulfonates, primary or secondary alkane sulfonates, alkyl sulfosuccinates, acyl taurates, acyl isethionates, alkyl glycerylether sulfonate, sulfonated methyl esters, sulfonated fatty acids, alkyl phosphates, acyl glutamates, acyl sarcosinates, alkyl sulfoacetates, acylated peptides, alkyl ether carboxylates, acyl lactylates, anionic fluorosurfactants, and combinations thereof.

Preferably, the anionic lathering surfactant includes alkyl sulfates, alkyl ether sulfates, alkyl glycerylether sulfonate, sodium cocoyl isethionate, sodium lauroyl sarcosinate and mixtures thereof. More preferably, the anionic lathering surfactant includes alkyl sulphates, alkyl ether sulfates, and alkanoyl sarcosinates. More preferably still, the anionic lathering surfactant includes laureth-2 sulfate, laureth-3 sulfate with ammonium or sodium counter-ions in each case, sodium lauroyl sarcosinate or mixtures thereof.

Personal cleansing compositions according to the invention may comprise from about 0.1% wt to about 30% wt anionic lathering surfactant, preferably from about 0.1% wt to about 25% wt, more preferably from about 0.1% wt to about 20% wt, even more preferably from about 0.1% wt to about 15% wt, more preferably still from about 2.5% wt to about 15% wt.

Amphoteric lathering surfactants which may be employed according to the invention include betaines, sultaines, hydroxysultaines, alkyliminoacetates, iminodialkanoates, aminoalkanoates, and mixtures thereof, preferably betaines, disodium lauroamphoacetates and sodium lauroamphoacetate, more preferably cocoamidopropyl betaine and sodium lauroamphoacetate.

Personal cleansing compositions according to the invention may comprise from about 0.1% wt to about 15% wt amphoteric lathering surfactant, preferably from about 0.1% wt to about 10% wt, more preferably from about 0.1% wt to about 8% wt, even more preferably from about 0.1% wt to about 7% wt more preferably still from about 1% wt to about 6.5% wt.

Nonionic lathering surfactants which may be employed according to the invention include alkyl glucosides, alkyl polyglucosides, polyhydroxy fatty acid amides, alkoxylated fatty acid esters, sucrose esters, amine oxides and mixtures thereof, preferably $C_8$-$C_{14}$ glucose amides, $C_8$-$C_{14}$ alkyl polyglucosides, sucrose cocoate, sucrose laurate, lauramine oxide, cocoamine oxide and mixtures thereof, more preferably still $C_8$-$C_{14}$ alkyl polyglucosides, lauramine oxide and mixtures thereof.

Personal cleansing compositions according to the invention may comprise from about 0.1% wt to about 10% wt nonionic lathering surfactant, preferably from about 0.1% wt to about 7.5% wt, more preferably from about 0.1% wt to about 5% wt, even more preferably from 0.1% wt to about 4% wt, more preferably still from about 0.1% wt to about 3% wt.

Cationic surfactants are generally not used alone, but in combination with other surfactants and the cationic surfactants may be lathering or non-lathering surfactants. Cationic surfactants which may be employed according to the invention include fatty amines, di-fatty quaternary amines, trifatty quaternary amines, imidazolinium quaternary amines, and combinations thereof, preferably cetyltrimethylammonium bromide, dialklamidoethyl hydroxyethylmonium methosulfate and mixtures thereof, more preferably cetyltrimethylammonium bromide.

Personal cleansing compositions according to the invention may comprise from about 0.1% wt to about 10% wt cationic surfactants, preferably from about 0.1% wt to 7.5% wt, more preferably from about 0.1% wt to 5% wt, even more preferably from about 0.1% wt to about 4% wt, yet more preferably from about 0.1% wt to about 3% wt.

As mentioned, the surfactant comprised within the personal cleansing compositions according to the invention advantageously comprises anionic and amphoteric lathering surfactant. Preferably, the ratio of anionic to amphoteric surfactant is from about 6:1 to about 1:3, more preferably from about 5:1 to about 1:3, even more preferably from about 4.5:1 to about 1:2, more preferably still from about 4:1 to about 1:2. Without wishing to be bound by theory, it is believed that, within these ranges, surfactant packing is increased thereby allowing formation of the second phase at lower perfume levels which increases fragrance deposition. In addition, within these ratio ranges, an increasingly improved balance of lather volume and mildness may be achieved.

Personal cleansing compositions according to the invention comprise Fragrance Oil. As referred to herein, the term "Fragrance Oil" refers to perfume materials which do not form an oil-in-water emulsion under the following conditions:

The following materials are weighed into an appropriate container: 8.0% Sodium Laureth 2 Sulfate, 3.0% Sodium Lauryl Sulfate, 3.0% Sodium Lauroyl Sarcosinate, 3.0% Cocamidopropyl Betaine, 0.5% Lauric Acid, and 2% Sodium Sulfate, 0.5% of the suspected Fragrance Oil, and QS water. The composition is then mixed using a Speed Mixer (DAC400 (Dual Asymmetric Centrifuge) FVZ, Flaktek Inc, Landrum, S.C.) for 1 minute at 2000 rpm, after which it is left to stand until de-aerated. Following this, the composition is observed under a light microscope (Microscope Nikon Eclipse E800, with a 10× Eyepiece, 20× objective lens). Fragrance Oils are those materials that do not form an oil-in-water emulsion when subjected to this test. An oil-in-water emulsion is easily identifiable to one skilled in the art. For the avoidance of doubt, the term "Fragrance Oil" may include single perfume raw materials.

(PRMs), i.e. materials comprising a single chemical, and mixtures of PRMs, provided that the Perfume Oil in question fulfils the above-defined requirement.

The personal cleansing compositions according to the invention may comprise from about 0.1% wt to about 5% wt Fragrance Oil, preferably from about 0.5% wt to about 5% wt, more preferably from about 0.5% wt to about 4.5% wt, even more preferably from about 1% wt to about 4.5% wt, more preferably still from about 1.5% wt to about 4% wt, yet more preferably from about 2% wt to about 4% wt.

A wide variety of chemicals may be employed as or included in the Fragrance Oil, including materials such as aldehydes, ketones and esters. More commonly, naturally occurring plant and animal oils and exudates comprising complex mixtures of various chemical components are known for use as or inclusion in Fragrance Oils.

Advantageously, every PRM comprised within the Fragrance Oil of the present invention has a boiling point (BP) of about 500° C. or lower, more preferably about 400° C. or lower. The BP of many PRMs are given in *Perfume and Flavor Chemicals (Aroma Chemicals)*, Steffen Arctander (1969), which is incorporated herein by reference.

Advantageously, The ClogP value every PRM comprised within the Fragrance Oil is greater than about 0.1, preferably greater than about 0.5, more preferably greater than about 1.0, even more preferably greater than about 1.2.

As used herein, the term "ClogP" in relation to a given material refers to the logarithm to the base 10 of the octanol/water partition coefficient of that material. This can be readily calculated from a program called "CLOGP" which is available from Daylight Chemical Information Systems Inc., Irvine Calif., USA. Octanol/water partition coefficients are described in more detail in U.S. Pat. No. 5,578,563, which is incorporated herein by reference.

Examples of Fragrance Oils useful herein include, but are not limited to, animal fragrances such as musk oil, civet, castoreum, ambergris, plant fragrances such as nutmeg extract, cardomon extract, ginger extract, cinnamon extract, patchouli oil, geranium oil, orange oil, mandarin oil, orange flower extract, cedarwood, vetyver, lavandin, ylang extract, tuberose extract, sandalwood oil, bergamot oil, rosemary oil, spearmint oil, peppermint oil, lemon oil, lavender oil, citronella oil, chamomille oil, clove oil, sage oil, neroli oil, labdanum oil, eucalyptus oil, verbena oil, mimosa extract, narcissus extract, carrot seed extract, jasmine extract, olibanum extract, rose extract and mixtures thereof.

Other examples of suitable Fragrance Oils include, but are not limited to, chemical substances such as acetophenone, adoxal, aldehyde C-12, aldehyde C-14, aldehyde C-18, allyl caprylate, ambroxan, amyl acetate, dimethylindane derivatives, α-amylcinnamic aldehyde, anethole, anisaldehyde, benzaldehyde, benzyl acetate, benzyl alcohol and ester derivatives, benzyl propionate, benzyl salicylate, borneol, butyl acetate, camphor, carbitol, cinnamaldehyde, cinnamyl acetate, cinnamyl alcohol, cis-3-hexanol and ester derivatives, cis-3-hexenyl methyl carbonate, citral, citronnellol and ester derivatives, cumin aldehyde, cyclamen aldehyde, cyclo galbanate, damascones, decalactone, decanol, estragole, dihydromyrcenol, dimethyl benzyl carbinol, 6,8-dimethyl-2-nonanol, dimethyl benzyl carbinyl butyrate, ethyl acetate, ethyl isobutyrate, ethyl butyrate, ethyl propionate, ethyl caprylate, ethyl cinnamate, ethyl hexanoate, ethyl valerate, ethyl vanillin, eugenol, exaltolide, fenchone, fruity esters such as ethyl 2-methyl butyrate, galaxolide, geraniol and ester derivatives, helional, 2-heptonone, hexenol, α-hexylcinnamic aldehyde, hydroxycitrolnellal, indole, isoamyl acetate, isoeugenol acetate, ionones, isoeugenol, isoamyl iso-valerate, iso E super, limonene, linalool, lilial, linalyl acetate, lyral, majantol, mayol, melonal, menthol, p-methylacetophenone, methyl anthranilate, methyl cedrylone, methyl dihydrojasmonate, methyl eugenol, methyl ionone, methyl-β-naphthyl ketone, methylphenylcarbinyl acetate, mugetanol, γ-nonalactone, octanal, phenyl ethyl acetate, phenyl-acetaldehyde dimethyl acetate, phenoxyethyl isobutyrate, phenyl ethyl alcohol, pinenes, sandalore, santalol, stemone, thymol, terpenes, triplal, triethyl citrate, 3,3,5-trimethylcyclohexanol, γ-undecalactone, undecenal, vanillin, veloutone, verdox and mixtures thereof.

Suitable Fragrance Oils can be found in U.S. Pat. Nos. 4,145,184, 4,209,417, 4,515,705, and 4,152,272, all of which are incorporated herein by reference.

As discussed above, the fragrance concentration at which the OTP occurs may be manipulated. This may be achieved by adding fatty alcohols, fatty acids, salts or mixtures thereof to the personal cleansing compositions according to the invention.

The personal cleansing compositions according to the invention may comprise fatty alcohol at a concentration from about 0.1% wt to about 4% wt, preferably from about 0.1% wt to about 3.5% wt, more preferably from about 0.1% wt to about 3% wt, more preferably still from about 0.1% wt to about 2.5% wt, yet more preferably from about 0.1% wt to about 2% wt, still more preferably from about 0.5% wt to about 2% wt. Preferably, the fatty alcohols comprise $C_8$-$C_{18}$ fatty alcohols, more preferably the fatty alcohol comprises lauryl alcohol.

The personal cleansing compositions according to the invention may comprise fatty acid at a concentration from about 0.1% wt to about 4% wt, preferably from about 0.1% wt to about 3.5% wt, more preferably from about 0.1% wt to about 3% wt, more preferably still from about 0.1% wt to about 2.5% wt, yet more preferably from about 0.1% wt to about 2% wt, still more preferably from about 0.5% wt to about 2% wt. Preferably, the fatty acid comprises $C_8$-$C_{18}$ fatty acid, more preferably the fatty acid comprises lauric acid.

The personal cleansing compositions according to the invention may comprise salt at a concentration from about 0.1% wt to about 8% wt, preferably from about 0.1% wt to about 6% wt, more preferably from about 0.1% wt to about 5% wt, more preferably still from about 0.1% wt to about 4% wt, yet more preferably from about 0.5% wt to about 4% wt, still more preferably from about 1% wt to about 4% wt. Preferably the salts comprise magnesium or sodium salts of sulfates or chlorides or mixtures thereof.

Personal cleansing compositions according to the invention may be formulated to have a pH in the range from 4 to 8, preferably from 4.5 to 7.5.

Personal cleansing compositions according to the invention may comprise Non-Fragrance Oil. As referred to herein, the term "Non-Fragrance Oil" refers to materials which form an oil-in-water emulsion under the following conditions:

The following materials are weighed into an appropriate container: 8.0% Sodium Laureth 2 Sulfate, 3.0% Sodium Lauryl Sulfate, 3.0% Sodium Lauroyl Sarcosinate, 3.0% Cocamidopropyl Betaine, 0.5% Lauric Acid, and 2% Sodium Sulfate, 0.5% of the suspected Fragrance Oil, and QS water. The composition is then mixed using a Speed Mixer (DAC400 (Dual Asymmetric Centrifuge) FVZ, Flaktek Inc, Landrum, S.C.) for 1 minute at 2000 rpm, after which it is left to stand until de-aerated. Following this, the composition is observed under a light microscope (Microscope Nikon Eclipse E800, with a 10× Eyepiece, 20× objective lens). Non-Fragrance Oils are those materials that form an oil-in-water emulsion when subjected to this test.

If personal cleansing compositions according to the invention comprise Non-Fragrance Oil, then it will be present as an oil-in-water emulsion. This emulsion may be stabilized by a lamellar surfactant phase that locates itself around the emulsion droplets, which lamellar surfactant phase typically will be able to rotate polarized light. Without wishing to be bound by theory, it is believed that the presence of this additional emulsion phase may decrease the amount of second (dispersed) phase formed. It is therefore preferred to minimize the amount of Non-Fragrance Oil present. Nevertheless, small quantities of Non-Fragrance Oil may provide skin benefits justifying their inclusion in some cases.

If present, the Non-Fragrance Oil may be derived form a natural source including animals, plants, or petroleum or from a synthetic source including silicone or hydrocarbons. Preferred oils are substantially water insoluble and substantially free from odor. Nonlimiting examples of Non-Fragrance Oils include those selected from the group consisting of mineral oil, petrolatum, lecithin, hydrogenated lecithin, lanolin, lanolin derivatives, $C_7$-$C_{40}$ branched chain hydrocarbons, $C_1$-$C_{30}$ alcohol esters of $C_1$-$C_{30}$ carboxylic acids, $C_1$-$C_{30}$ alcohol esters of $C_2$-$C_{30}$ dicarboxylic acids, monoglycerides of $C_1$-$C_{30}$ carboxylic acids, diglycerides of $C_1$-$C_{30}$ carboxylic acids, triglycerides of $C_1$-$C_{30}$ carboxylic acids, ethylene glycol monoesters of $C_1$-$C_{30}$ carboxylic acids, ethylene glycol diesters of $C_1$-$C_{30}$ carboxylic acids, propylene glycol monoesters of $C_1$-$C_{30}$ carboxylic acids, propylene glycol diesters of $C_1$-$C_{30}$ carboxylic acids, $C_1$-$C_{30}$ carboxylic acid monoesters and polyesters of sugars, polydialkylsiloxanes, polydiarylsiloxanes, polyalkarylsiloxanes, cylcomethicones having 3 to 9 silicon atoms, vegetable oils, hydrogenated vegetable oils, polypropylene glycol $C_4$-$C_{20}$ alkyl ethers, di $C_8$-$C_{30}$ alkyl ethers, poly-alpha-olefins and combinations thereof.

Preferably, the personal cleansing compositions according to the invention comprise less than about 7% wt Non-Fragrance Oil, more preferably less than about 5% wt, more preferably still less than about 3% wt, yet more preferably less than about 1% wt and even more preferably no Non-Fragrance Oil.

Personal cleansing compositions according to the invention may also comprise hydrophilic conditioning agents. Nonlimiting examples of hydrophilic conditioning agents which may be included in personal cleansing compositions according to the invention include those selected from the group consisting of polyhydric alcohols, polypropylene glycols, polyethylene glycols, ureas, pyrolidone carboxylic acids, ethoxylated and/or propoxylated $C_3$-$C_6$ diols and triols, alpha-hydroxy $C_2$-$C_2$ carboxylic acids, ethoxylated and/or propoxylated sugars, polyacrylic acid copolymers, sugars having up to about 12 carbons atoms, sugar alcohols having up to about 12 carbon atoms, and mixtures thereof. Specific examples of useful hydrophilic conditioning agents include materials such as urea; guanidine; glycolic acid and glycolate salts (e.g., ammonium and quaternary alkyl ammonium); lactic acid and lactate salts (e.g., ammonium and quaternary alkyl ammonium); sucrose, fructose, glucose, eruthrose, erythritol, sorbitol, mannitol, glycerol, hexanetriol, propylene glycol, butylene glycol, hexylene glycol, and the like; polyethylene glycols such as PEG-2, PEG-3, PEG-30, PEG-50, polypropylene glycols such as PPG-9, PPG-12, PPG-15, PPG-17, PPG-20, PPG-26, PPG-30, PPG-34; alkoxylated glucose; hyaluronic acid; cationic skin conditioning polymers (e.g., quaternary ammonium polymers such as Polyquaternium polymers); and mixtures thereof. Glycerol is a preferred hydrophilic conditioning agent in the articles of the present invention.

Personal cleansing compositions according to the invention may additionally comprise cationic or anionic polymers or mixtures of these materials.

The cationic polymers may be selected from the group consisting of natural backbone quaternary ammonium polymers, synthetic backbone quaternary ammonium polymers, natural backbone amphoteric type polymers, synthetic backbone amphoteric type polymers, and combinations thereof. Preferably, the cationic polymer is a quaternary ammonium polymer. More preferably, the cationic polymer is a natural backbone quaternary ammonium polymer. Even more preferably the cationic polymer is a polyquaternium 10, polyquaternium 7, polyquaternium 37 or a guar derivative.

Anionic polymers may also be included in the composition. These may be selected from the group consisting of polyacrylic acid polymers, polyacrylamide polymers, copolymers of acrylic acid, acrylamide, and other natural or synthetic polymers.

Personal cleansing compositions according to the invention may also comprise stabilisers, such as, without limitation, polymeric thickeners, crystalline stabilising agents including trihydroxystearin, and mixtures thereof.

Personal cleansing compositions according to the invention may also comprise vitamins and derivatives thereof, sunscreens, preservatives, chelators and sequestrants and aesthetic agents such as dyes, mica, titanium dioxide, ethylene glycol distearate (EGDS).

Personal cleansing compositions according to the present invention exhibit specific physical properties, which may be demonstrated by appropriate test methods performed on the entire composition. In some circumstances, however, such as those in which a stabiliser network, an opacifier or an emulsion is present in the personal cleansing composition, tests performed on the entire composition may not yield accurate results. In those cases, it is appropriate to perform tests on only a portion of the composition. Both types of test method are presented hereinbelow.

Tests on the Entire Personal Cleansing Composition

Microscopy Test for Birefringence

The Light Microscopy technique allows gross visualisation of the surfactant phases within a composition.

In order to observe the gross surfactant structure by light microscopy, a 10 µl sample of the composition is placed onto a glass microscope slide. A cover slip is placed on top of the sample of the composition. The sample is then placed onto the microscope stand (Microscope Nikon Eclipse E800, with a 10× Eyepiece). Using the 20× objective lens, the sample of the composition is observed and the images are recorded. Once the sample of the composition has been observed using non-polarized light microscopy, it is then observed using polarized light. With the polarizer (present between the light source and the specimen stage) set in the East-West direction and the analyzer (present between the specimen stage and the observer) aligned in the North-South direction, the sample is observed. Those parts of the sample which are able to rotate light will result in an image with birefringence.

Compositions according to the invention have a second phase dispersed among a first micellar phase. The first micellar phase is observed as a clear phase under light microscopy at ×200, when no opacifiers or liquid crystalline stabilizers are present. Under polarized light this phase does not transmit light. The second dispersed phase is birefringent when viewed under polarized light. This method can also be used after the composition has been centrifuged or separated by other means, where distinct portions including phases of the composition can be looked at individually. In this case, one phase would be expected to exhibit birefringence and one not.

Cryo-TEM Test

The Cryo-Transmission Electron Microscopy technique (cryo-TEM) allows visualization of microstructures of surfactant phases within a composition. Without wishing to be limited by theory, it is believed that surfactant phase microstructure may be a principal determinant of the efficiency of perfume delivery in the compositions according to the invention.

In order to observe the surfactant microstructures by cryo-TEM, the samples are prepared in a controlled environment vitrification system (CEVS)—see Bellare, J. R.; Davis, H. T.; Scriven, L. E.; Talmon, Y., *Controlled environment vitrification technique, J. Electron Microsc. Tech.*, 1988, 10, 87-111, which is incorporated herein by reference. A 2 µl sample of the composition is placed on a carbon-coated holey polymer support film mounted on a standard 300-mesh TEM grid (Ted Pella, Inc.). The sample of the composition is blotted with filter paper until it is reduced to a thin film (10-300 nm) spanning the holes (2-8 µm) of the support film. The sample of the composition is then vitrified by rapidly plunging it through a synchronous shutter at the bottom of the CEVS into liquid ethane at its freezing point. The vitreous specimen of the composition is transferred under liquid nitrogen into a Philips CM120 transmission electron microscope for imaging. The temperature of the sample of the composition is kept under −175° C. throughout the examination. The digital images are recorded with embedded scale bars for determining the dimensions of microstructures.

Compositions according to the invention exhibit a second phase dispersed among a first micellar phase. Generally, the first micellar phase is observed as either a phase primarily containing worm-like micelles or a sponge phase under cryo-TEM. Generally, the second (dispersed) phase is observed to consist principally of multi-lamellar vesicles.

Turbidity Test on Addition of Fragrance to the Personal Cleansing Composition

This test measures the change in turbidity on addition of the fragrance, Para Cresyl Methyl Ether, to a personal cleansing composition. Turbidity change is a principal indicator of the formation of a second phase in response to perfume addition. This second phase is generated above the Opacity Transition Point.

In order to measure the change in turbidity on addition of fragrance, 100 g of a personal cleansing composition according to the invention is weighed into an appropriate receptacle, 0.5% weight of fragrance (Para Cresyl Methyl Ether) is added thereto and the composition is mixed using a Speed Mixer (DAC400 (Dual Asymmetric Centrifuge) FVZ, Flaktek Inc, Landrum, S.C.) for 1 minute at 2000 rpm. The composition is left to stand for 24 hours to eliminate any air bubbles. After 24 hours, the turbidity of the personal cleansing composition prior to fragrance addition, and the turbidity of the personal cleansing composition plus fragrance are measured.

To measure the turbidity of the compositions, the Mettler Toledo FSC402 Process Turbidity Meter is calibrated. Turbidity is measured using a Mettler Toledo FSC402, Process Turbidity Meter using back scattering, or equivalent, which measures relative turbidity from 0 to 100% as described herein. To calibrate this instrument, 100 g white gloss latex paint or equivalent (Everwhite, Non-Yellowing, Low Odour Gloss, Supplied by B&Q, UK) is placed into a 120 ml Beatson Clark Glass Jar (Base diameter; 6 cm, Top diameter; 5.2 cm, Height to Bottom of Screw Lip; 5 cm). The probe is slowly inserted into the paint to minimize formation of air bubbles, ensuring that the top of the probe is 4 cm from the base of the jar. White gloss paint is calibrated as 100% turbidity. Next, the probe is cleaned with ethanol and 10 g DI Water poured into a 120 ml Beatson Clark Glass Jar (base diameter; 6 cm, top diameter; 5.2 cm, height to bottom of screw lip; 5 cm). The probe is inserted slowly into the water, ensuring that the top of the probe is 4 cm from the base of the jar. De-ionised water is calibrated as 0% Turbidity. The probe is cleaned with ethanol after each reading. The "Gain" is recorded each time the instrument is used and it is ensured that this remains constant each time the instrument is used. Calibration is now complete.

All compositions should be stored at 25° C. prior to turbidity readings being taken to minimize error.

This method employs a specific perfume raw material, Para Cresyl Methyl Ether.

In order to measure the change in turbidity on addition of fragrance, 100 g of the personal cleansing composition is weighed into a 120 ml Beatson Clark Glass Jar (base diameter; 6 cm, top diameter; 5.2 cm, height to bottom of screw lip; 5 cm). The probe is slowly inserted into the composition to minimize formation of air bubbles, ensuring that the top of the probe is 4 cm from the base of the jar. A reading is taken once the display has settled, then a second reading is taken after 60 seconds. An average of these two readings is recorded. Turbidity readings are in % Turbidity.

This procedure is repeated to determine the turbidity of the composition plus fragrance.

Preferred compositions of the present invention are characterised by undergoing a turbidity increase on addition of fragrance to the composition (as defined above), of greater than 5%, preferably greater than 10%, more preferably greater than 15%, more preferably still greater than 20%, yet more preferably greater than 25%. For the avoidance of doubt, the percentage turbidity increase is calculated by subtracting the % turbidity value of the personal cleansing composition alone, from the % turbidity value of the personal cleansing composition with added fragrance.

Lather

The lather test assesses the amount of lather produced from a personal cleansing composition. High lathering, high fragrance-depositing compositions are unusual. Without wishing to be bound by theory, it is believed that this is due to the interference of the fragrance and/or the fragrance-depositing component with lather. Surprisingly, personal cleansing compositions according to the present invention are capable of producing a high degree of lather. For the avoidance of doubt, it is the combination of high lather with high fragrance deposition which is unusual, which does not necessarily mean that high levels of fragrance per se have to be present. However, for perfume levels of more than about 1.5% wt, preferably more than about 2% wt, surprisingly high lather benefits and high perfume deposition are observed.

In order to conduct the lather test 0.5 g of the personal cleansing composition is weighed into a 500 ml glass cylinder (Supplied by E-MIL, England, ISO 4788, 5 cm internal diameter, 36 cm height). 50 g de-ionised water is added and the cylinder top is sealed with film (Nescofilm, Bando Chemicals, Japan). A hand is clasped over the top of the cylinder (to support the film) and the cylinder is rotated 90° to the right hand side, returned to the original position and repeated 30 times in 60 seconds. Once complete, the cylinder is returned to the worktop. Using a palette knife, the cylinder sides are scraped, pushing down the lather to the point at which the lather forms a continuous film across the cylinder diameter. Using a ruler, the lather height is measured.

Personal cleansing compositions according to the invention have a lather volume of greater than 150 ml (7.8 cm), preferably greater than 200 ml (10.4 cm), more preferably greater than 250 ml (13.2 cm), more preferably still greater than 300 ml (15.8 cm).

Methods for Separating Clear and Opaque Components from the Personal Cleansing Composition The tests below require the clear and opaque components of the personal cleansing composition to be separated into distinct phases using centrifugation.

A clear component as described herein is one having a turbidity <10% using the Mettler Toledo FSC402, Process Turbidity Meter) and an opaque component described herein is one having a turbidity >10% using the Mettler Toledo FSC402, Process Turbidity Meter.

Advantageously, the opaque phase is less dense than the clear phase (i.e. higher in the centrifuge tube).

Where centrifugation is used to separate the phases, 30 g of the composition is weighed into a Beckman-Nalgene Centrifuge tube (10 cm height, 2.9 cm diameter). The number of samples of the composition required is determined by the amount of opaque and clear phase that is eventually harvested after centrifugation. The composition is spun on a centrifuge (Beckman, Avanti 30 Centrifuge) for 31.5 hours, at 30° C., 16000 rpm, Average G-Force=19000 RCF (G), where RCF stands for Relative Centrifugal Force, Maximum G-Force=27000RCF (G). The composition is observed for the presence of a clear component (defined as having a turbidity <10% using the Mettler Toledo FSC402, Process Turbidity Meter) and an opaque component (defined as having a turbidity >10% using the Mettler Toledo FSC402, Process Turbidity Meter.

When stabiliser networks, opacifiers or emulsions are present, an opaque component and clear component, as defined above, are not observed. In those cases, the sample can be ultra-centrifuged (Beckman optima XL-100K Ultracentrifuge) for 48 hours at 30° C., 90,000 rpm, Average G-Force=502100 RCF (G), where RCF stands for Relative Centrifugal Force, Maximum G-Force=694000 RCF (G).

In some cases, where stabiliser networks, are present in a composition, the composition cannot be fully separated by centrifugation or ultra-centrifugation. In addition to this, the stabiliser networks, opacifiers or emulsions may interfere with turbidity readings. In these cases, the below-defined methods may be used to separate the opaque and clear components of the composition.

(a) Destruction of the Stabiliser Network by Heating: a 500 g sample of the personal cleansing composition is weighed into a suitable container, an overhead paddle blade is lowered into the container and mixing commenced. The container is covered with foil and the sample is heated to 92° C. whilst mixing gently with the overhead mixer. The composition is held at 92° C. for 2 minutes and rapidly cooled to room temperature using an ice bath at a rate of 5° C./minute. The composition is then allowed to stand for 24 hours after which it is centrifuged (as defined above) and the separate opaque and clear components are extracted, as defined above.

(b) Destruction of the Stabiliser Network by Milling: a 500 g sample of the personal cleansing composition is weighed into a suitable container. The head (fine tipped) of the Ultra Turrax T50 milling device (Janke & Kunkel, IKA Labortechnik) is lowered into the sample which is then milled for 5 minutes at 10,000 rpm. The composition is then allowed to stand for 24 hours after which it is centrifuged (as defined above) and the separate opaque and clear components are extracted as defined above.

After subjecting a personal cleansing composition to the above separation methods, it will comprise two or more components of differing clarity. Where there are more than two such components, the clearest of these shall be referred to herein as the "clear component" and the most opaque of these components shall be described as the "opaque component".

Tests on Portions of the Clear and Opaque Components of the Personal Cleansing Composition Light Microscopy The method used for this test is identical to the one described as the "Light microscopy test", above, in relation to the entire composition. When viewed under polarized light, the clear component is observed as a clear phase under light microscopy at x200. Under polarized light this phase does not transmit light. The opaque component is birefringent when viewed under polarized light.

Cryo-TEM Test

The method used for this test is identical to the one described in the "Cryo-TEM test", above, in relation to the entire composition. The clear component is observed as a phase primarily containing worm-like micelles or a sponge phase under cryo-TEM. Generally, the opaque component is observed to consist principally of multi-lamellar vesicles.

Turbidity Test on Addition of Fragrance to the Clear Component

This test measures the change in turbidity on addition of the fragrance, Para Cresyl Methyl Ether, to the clear component of the personal cleansing composition. Turbidity change is a principal indicator of the formation of a second phase in response to perfume addition, at and above the OTP. If a personal cleansing composition contains sufficient perfume for it to be above its OTP (i.e. for it to have an opaque phase), then the clear component will be saturated with perfume. The addition of additional fragrance to the clear component will therefore result in a turbidity change in the clear component as well, caused by the clear component being pushed above its own OTP. This further turbidity change only occurs when the clear component of a composition is saturated with perfume and demonstrates that the entire personal cleansing composition is above the OTP.

The method used for this test is identical to the one described in the "Turbidity test on addition of fragrance to the personal cleansing composition" section. Preferred compositions of the present invention have a clear component that is characterised by undergoing a turbidity increase on addition of fragrance to the composition (as defined above), of greater than 2.5%, preferably greater than 5%, more preferably greater than 10%, more preferably still greater than 15%, yet more preferably greater than 20%. For the avoidance of doubt, the percentage turbidity increase is calculated by subtracting the % turbidity value of the personal cleansing composition alone, from the % turbidity value of the personal cleansing composition with added fragrance.

Component Viscosity Test

The Component Viscosity Test measures the difference in viscosity between the opaque component and the clear component of a composition Viscosity is a principal indicator of the presence of a second phase, and also indicates how well a phase may deposit onto a substrate, such as skin or hair, during rinsing.

To measure the viscosity of the components, 2.5 ml of the opaque component is placed onto the plate of an AR1000 Rheolyst TA Instruments Rheometer. Using a 6 cm, 2° C. degree acrylic cone, with a gap set at 75 µm and the shear rate set to 1/s, the viscosity (Pas) is measured at a shear rate of 1/s and a temperature of 25° C. This information is gathered five times for one sample of the composition and an average viscosity is calculated. This procedure is repeated for a second product sample of the composition.

This procedure is repeated to determine the viscosity of the clear component.

Personal cleansing compositions according to the present invention have an opaque component which has a higher viscosity than the clear component. Preferably the opaque component has a viscosity from about 3 Pas to about 47.5 Pas, more preferably from about 3.5 Pas to about 45 Pas, more preferably still from about 4 Pas to about 40 Pas, yet more preferably from about 4 Pas to about 35 Pas, even more preferably from about 4 Pas to about 30 Pas.

The clear component of the composition has a viscosity of less than about 10 Pas, preferably less than about 9 Pas, more preferably less than about 8 Pas, more preferably still less than about 7 Pas, yet more preferably less than about 6 Pas.

Fragrance Enrichment Test

This test assesses how much fragrance is concentrated in each component of a personal cleansing composition according to the invention. As discussed above, the second phase (opaque component) is perfume enriched in comparison with the first micellar phase (clear component), so a comparison of the perfume concentrations of these two phases demonstrates the existence of these two phases.

2 g of the clear component is placed into a glass vial containing 10 ml of dichloromethane and 2 g of sodium chloride. The sample of the clear component is shaken vigorously to mix and allowed to separate into an aqueous and an organic layer. The dichloromethane layer is sampled and analysis is done by GC separation with FID detection [0.25 um (5% phenyl)-methylpolysiloxane, 100° C./10'/250° C./5']. The total level of perfume is calculated using a standard solution of the perfume, or, where the standard is not available, mass spectroscopy is carried out to determine the level of perfume present. This method calculates total concentration of known perfume materials in a composition and shows typical standard deviations of 10%.

An identical procedure is used to determine the total level of perfume in the opaque component.

Personal cleansing compositions according to the present invention comprise a perfume-enriched opaque component and a perfume-depleted clear component. By perfume enriched we mean that the ratio of the perfume weight percentage in the opaque component to the ratio of the perfume weight percentage in the clear component is greater than about 1, preferably greater than about 1.25, more preferably greater than about 1.5, more preferably still greater than about 1.75, yet more preferably greater than about 2.

EXAMPLES

The below exemplified personal cleansing compositions according to the invention may be made using the methods outlined hereinbelow.

The trihydroxystearin-surfactant premix is used in examples that include trihydroxystearin.

Trihydroxystearin—Surfactant Premix
(1) Weigh the surfactants (selected from Sodium Laureth-3 Sulfate, Sodium Laureth-2 Sulfate, Sodium Lauryl Sulfate, Cocamidopropyl betaine, Sodium LauroAmphoacetate, Cocamide MEA) in to a suitable vessel.
(2) Commence heating to 92° C., whilst mixing with a medium agitation speed.
(3) At 60° C., add the lauric acid and lauryl alcohol, continue to mix
(4) At 90° C., add the trihydroxystearin and continue to mix until the trihydroxystearin is molten and dissolved (92° C.)
(5) Cool to room temperature.
(6) Add EDTA and Benzoate to the mixture and slow cool the second vessel to room temperature whilst mixing.
(7) At <40° C., add DMDM Hydantoin and mix for a further 5 minutes under low agitation.
(8) Once at Room temperature stop mixing.

Method of Making for Examples Using N-Hance 3196 and Polyguaternium 10
(1) Weigh water into a suitable vessel and start mixing with low agitation
(2) Slowly disperse the polymer (selected from N-Hance 3196 or Polyquatemium 10) into the water and mix for 20 minutes.
(3) Once the polymer is hydrated, slowly add the trihydroxystearin-surfactant premix whilst mixing. Also add at this stage any additional surfactants (sodium lauroyl sarcosinate where included). Allow to mix for approximately 30 minutes, until the composition is homogeneous.
(4) Slowly add sodium sulfate or sodium chloride (as defined in the example), and allow to mix for an additional 20 minutes.
(5) Add perfume, dyes and EGDS to the composition and mix for 30 minutes.
(6) Adjust the pH to the specified limit, mix for a further 20 minutes Method of Making for Examples Using Carbopol EDTD2020
(1) Weigh water into a suitable vessel and start mixing with low agitation
(2) Slowly disperse the polymer (Carbopol EDTD2020) into the water and mix for 20 minutes.
(3) Adjust pH with sodium hydroxide solution to pH8. The polymer will begin to swell. Heat to 40° C. whilst mixing and ensure the polymer is fully hydrated. Cool the polymer premix to room temperature.
(4) Continue mixing the polymer premix and add the surfactants (selected from Sodium Laureth-3 Sulfate, Sodium Laureth-2 Sulfate, Sodium Lauryl Sulfate, Cocamidopropyl betaine, Sodium LauroAmphoacetate, Cocamide MEA and Sodium Lauryl Sarcosinate where included). Allow to mix for approximately 30 minutes, until the composition is homogeneous.
(5) Slowly add sodium sulfate or sodium chloride (as defined in the example), and allow to mix for an additional 20 minutes.
(6) Add perfume, dyes and EGDS to the composition and mix for 30 minutes.
(7) Adjust the pH to the specified limit, mix for a further 20 minutes

| INGREDIENT CHEMICAL/INCI NAME | Example 1 | Example 2 | Example 3 | Example 4 |
|---|---|---|---|---|
| Water | qs | qs | Qs | qs |
| Sodium Laureth 3 Sulphate | 10.5000 | 10.5000 | | 11.0000 |
| Sodium Laureth 2 Sulphate | | | 8.0000 | |
| Sodium Lauryl Sulfate | | | 3.0000 | |
| Ammonium Lauryl Sulfate | | | | |
| Ammonium Laureth 3 Sulfate | | | | |
| Cocamidopropyl Betaine | 3.0000 | 4.0000 | 3.0000 | 5.5000 |
| Sodium Lauroyl Sarcosinate | 3.0000 | 3.0000 | 3.0000 | 1.5000 |
| Sodium Lauroamphoacetate | | | | |
| Cocamido MEA | | | | |
| Trihydroxystearin | 1.5000 | 0.5000 | 0.5000 | 0.5000 |
| Carbopol EDTD2020 | | | | |
| N-Hance 3196 | | | | |
| Polyquaternium-10[1] | 0.1000 | 0.1000 | | |
| Polyquaternium-10[2] | | | 0.2000 | 0.1000 |
| Polyquaternium-10[3] | | | | |
| PEG 7M | | | | |
| Citric Acid | Max 1 | Max 1 | Max 1 | Max 1 |
| Sodium Hydroxide | Max 0.3 | Max 0.3 | Max 0.3 | Max 0.3 |
| Sodium Sulfate | 3.0000 | 4.0000 | 4.0000 | 2.0000 |
| Sodium Chloride | | | | |
| Tetrasodium EDTA | 0.1500 | 0.1500 | 0.1500 | 0.1500 |
| Sodium Benzoate | 0.2500 | 0.2500 | 0.2500 | 0.2500 |
| DMDM Hydantion | 0.2000 | 0.2000 | 0.2000 | 0.2000 |
| Lauric Acid | 1.5000 | 1.5000 | 1.5000 | 1.5000 |
| Lauryl Alcohol | | | | |

-continued

| INGREDIENT CHEMICAL/INCI NAME | | | | |
|---|---|---|---|---|
| Cetyl Alcohol | | | | |
| Perfume | 4.9000 | 1.5000 | 2.0000 | 4.0000 |
| Glycerin | | | | |
| Petrolatum | | | | |
| Soy Bean oil | | | | |
| Hydrogenated Polydecene | | | | |
| D&C Red 33 | 0.0003 | 0.0003 | | 0.0003 |
| FD&C Green 3 | 0.0001 | 0.0001 | | 0.0001 |
| EGDS | 2.0000 | 2.0000 | 2.0000 | 2.0000 |
| pH | 5.5000 | 6 | 5.5 | 6.5 |

| INGREDIENT CHEMICAL/INCI NAME | Example 5 | Example 6 | Example 7 | Example 8 |
|---|---|---|---|---|
| Water | qs | qs | qs | qs |
| Sodium Laureth 3 Sulphate | 7.5000 | | 5.5000 | |
| Sodium Laureth 2 Sulphate | | 10.0000 | | |
| Sodium Lauryl Sulfate | | | | |
| Ammonium Lauryl Sulfate | | | | |
| Ammonium Laureth 3 Sulfate | | | | 10.0000 |
| Cocamidopropyl Betaine | 6.5000 | 2.8000 | 5.0000 | 2.0000 |
| Sodium Lauroyl Sarcosinate | 3.0000 | | 0.5000 | |
| Sodium Lauroamphoacetate | | | | 1.0000 |
| Cocamido MEA | | | | |
| Trihydroxystearin | 1.5000 | 1.0000 | 0.5000 | 0.3000 |
| Carbopol EDTD2020 | | | | |
| N-Hance 3196 | | | | |
| Polyquaternium-10[1] | 0.0500 | | 0.1000 | 0.2000 |
| Polyquaternium-10[2] | 0.0500 | 0.0500 | | 0.0000 |
| Polyquaternium-10[3] | | | | |
| PEG 7M | | | | |
| Citric Acid | Max 1 | Max 1 | Max 1 | Max 1 |
| Sodium Hydroxide | Max 0.3 | Max 0.3 | Max 0.3 | Max 0.3 |
| Sodium Sulfate | 4.0000 | 2.0000 | 4.0000 | 4.0000 |
| Sodium Chloride | | | | |
| Tetrasodium EDTA | 0.1500 | 0.1500 | 0.1500 | 0.1500 |
| Sodium Benzoate | 0.2500 | 0.2500 | 0.2500 | 0.2500 |
| DMDM Hydantion | 0.2000 | 0.2000 | 0.2000 | 0.2000 |
| Lauric Acid | 1.0000 | 1.0000 | | 1.0000 |
| Lauryl Alcohol | | | 1.0000 | |
| Cetyl Alcohol | | | | |
| Perfume | 4.0000 | 2.0000 | 1.5000 | 2.0000 |
| Glycerin | | | | 1.0000 |
| Petrolatum | | | | |
| Soy Bean oil | | | | |
| Hydrogenated Polydecene | | | | |
| D&C Red 33 | 0.0003 | | | 0.0003 |
| FD&C Green 3 | 0.0001 | | | 0.0001 |
| EGDS | 2.0000 | 2.0000 | | 2.0000 |
| pH | 6 | 6.25 | 5 | 5.5 |

| INGREDIENT CHEMICAL/INCI NAME | Ex. 9 | Ex. 10 | Ex. 11 | Ex. 12 | Ex. 13 | Ex. 14 |
|---|---|---|---|---|---|---|
| Water | qs | qs | qs | qs | qs | qs |
| Sodium Laureth 3 Sulphate | | | 10.0000 | 13.0000 | | |
| Sodium Laureth 2 Sulphate | | | | | | |
| Sodium Lauryl Sulfate | | | | 4 | | |
| Ammonium Lauryl Sulfate | 4.2000 | 3.5000 | | | | 8.0000 |
| Ammonium Laureth 3 Sulfate | 7.5000 | 6.0000 | | | | 12.0000 |
| Cocamidopropyl Betaine | | | | | 15.0000 | |
| Sodium Lauroyl Sarcosinate | | | | 0.5000 | | |
| Sodium Lauroamphoacetate | | 4.5000 | 3.5000 | | 3.0000 | |
| Cocamido MEA | 1.0000 | | 3.0000 | | 1.0000 | 1.0000 |
| Trihydroxystearin | 0.5000 | 0.5000 | | 0.3000 | 0.5000 | |
| Carbopol EDTD2020 | | | 0.5000 | | | |
| N-Hance 3196 | 0.2000 | 0.7500 | | 0.7500 | | |
| Polyquaternium-10[1] | | | 0.5000 | | 0.1000 | |
| Polyquaternium-10[2] | | 0.1000 | | | | |
| Polyquaternium-10[3] | | | | | | 0.5000 |
| PEG 7M | | | | | | 0.1000 |
| Citric Acid | Max 1 | Max 2 | Max 2 | Max 2 | Max 2 | Max 1 |
| Sodium Hydroxide | Max 0.3 | Max 0.4 | Max 0.4 | Max 0.4 | Max 0.4 | Max 0.3 |
| Sodium Sulfate | 3.0000 | | | 3.5000 | 4.0000 | |
| Sodium Chloride | | 1.0000 | 0.7500 | | | 1.5000 |
| Tetrasodium EDTA | 0.1500 | 0.1500 | 0.1500 | 0.1500 | 0.1500 | 0.1300 |
| Sodium Benzoate | 0.2500 | 0.2500 | 0.2500 | 0.2500 | 0.2500 | 0.2500 |
| DMDM Hydantion | 0.2000 | 0.2000 | 0.2000 | 0.2000 | 0.2000 | 0.0500 |
| Lauric Acid | 0.5000 | 1.7500 | 2.5000 | 1.5000 | 0.7500 | 0.5000 |

-continued

| | | | | | | |
|---|---|---|---|---|---|---|
| Lauryl Alcohol | | | | | | |
| Cetyl Alcohol | | | | | | 1.0000 |
| Perfume | 2.5000 | 2.0000 | 3.0000 | 4.0000 | 3.5000 | 2.0000 |
| Glycerin | | | 3.0000 | | | |
| Petrolatum | | 7.4000 | | | | |
| Soy Bean oil | | | 7.4000 | | | |
| Hydrogenated Polydecene | | | | | | 0.3000 |
| D&C Red 33 | | | 0.0003 | | | |
| FD&C Green 3 | | | 0.0001 | | | |
| EGDS | 2.0000 | | 2.0000 | 2.0000 | 2.0000 | 1.5000 |
| PH | 6 | 5.5 | 5.5 | 7 | 6 | 6 |

| INGREDIENT CHEMICAL/ INCI NAME | TRADE NAME | SUPPLIER |
|---|---|---|
| Sodium Laureth Sulfate | Agent 1737-96 A | Stepan |
| Sodium Lauryl Sulfate | | |
| Cocoamidopropyl Betaine | | Goldschmidt-Degussa |
| Sodium Laureth 3 Sulphate | Empicol ESC70, | Huntsman |
| Sodium Laureth 3 Sulphate | Steol CS330 | Stepan |
| Sodium Laureth 2 Sulphate | Empicol ESB70, | Huntsman |
| Ammonium Lauryl Sulfate | Ammonium Lauryl Sulfate | Manro, Stalybridge, UK |
| Ammonium Laureth 3 Sulfate | Ammonium Laureth 3 Sulfate | Manro, Stalybridge, UK |
| Sodium Lauroamphoacetate | Miranol Ultra L32 | Rhodia |
| Cocamidopropyl Betaine | Tego Betain-F | Goldschmidt-Degussa |
| Sodium Lauroyl Sarcosinate | Hamposyl L-95, Hamposyl L30 | Dow |
| Cocamide MEA | Monamid CMA | Uniqema, Patterson, NJ |
| Carbopol EDTD2020 | Acrylates/C10–30 Alkyl Acrylate Crosspolymer | Noveon Inc |
| Guar Hydroxy Propyl Trimonium Chloride | N-Hance 3196 | Hercules |
| Polyquaternium-10[1] | Polymer JR30M | Amerchol Corp, Edison, N.J USA |
| Polyquaternium-10[2] | Polymer KG30M | Amerchol Corp, Edison, N.J USA |
| Polyquaternium-10[3] | Polymer LR400 | Amerchol Corp, Edison, N.J USA |
| Citric Acid | Citric Acid | Roche |
| Sodium Hydroxide | Sodium Hydroxide | |
| Sodium Sulfate | Sodium Sulfate | Ashland/Giles Chemicals |
| Sodium Chloride | Sodium Chloride | Cargill Salt/Breaux Bridge, Louisiana |
| Trihydroxystearin | Thixcin-R | Rheox Inc |
| EGDS | Tegopearl N-100 | Goldschmidt-Degussa |
| Tetrasodium EDTA | Dissolvine 220S | Akzo Nobel |
| Sodium Benzoate | Sodium Benzoate | Merck GmbH |
| DMDM Hydantion | Glydant 55 | Lonza |
| Lauric Acid | Emery 652 | Cognis |
| PEG 7M | Polyox WSR N-750 | Amerchol Corp, Edison, N.J USA |
| Hydrogenated Polydecene | SynFluid PAO 6 cst | Chevron Philips Chemical Co, Texas, USA |
| Cetyl Alcohol | Cetyl Alcohol | Goldschmidt-Degussa |
| D&C Red 33 | D&C Red 34 | Sensient (Warner Jenkinson (LCW), 2526 Baldwin Road, St Louis, Mo.63105 |
| FD&C Green 3 | FD&C Green 3, WJ#6503 | Sensient (Warner Jenkinson (LCW), 2526 Baldwin Road, St Louis, Mo.63106 |
| Glycerin | Glycerin | P&G Chemicals |
| Petrolatum | Super White Protopet | CK Witco |
| Soy Bean Oil | Ceraphyl NGA | ISP Van Dyk, Freetown Fine Chemicals Plant, Assonet, MA |
| Perfume | Perfume | Various |

It is understood that the examples and embodiments described herein are for illustrative purposes only and that various modifications or changes in light thereof will be suggested to one skilled in the art without departing from the scope of the present invention.

All documents cited in the Detailed Description of the Invention are, in relevant part, incorporated herein by reference; the citation of any document is not to be construed as an admission that it is prior art with respect to the present invention.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A personal cleaning composition comprising
    a) a surfactant matrix comprising from about 11.0% wt to 18% wt of a mixture of surfactants comprising:
        i. an anionic surfactant;
        ii. an amphoteric surfactant;
            wherein the ratio of anionic surfactant to amphoteric surfactant is from about 6:1 to about 1:3;
    b) from about 1.5% wt to about 5% wt a fragrance oil;

c) a material selected from fatty acid, fatty alcohol, salt and mixtures thereof; and trihydroxystearin;

wherein upon the addition of the fragrance oil to the surfactant matrix, the personal cleaning composition comprises a) a first micellar phase; and b) a second opaque phase which rotates polarized light;

with the proviso that the surfactant matrix is free from a hydrophobic silicone phase; and wherein the personal cleaning composition has a lather volume of greater than 150 mL.

2. The personal cleansing composition of claim 1, wherein the ratio of anionic to amphoteric surfactant is from about 4:1 to about 1:2.

3. The personal cleansing composition of claim 1, wherein the ratio of anionic to amphoteric surfactant is from about 4.5:1 to about 1:2.

4. The personal cleansing composition of claim 1 comprising from about 0.1% wt to about 5% wt fragrance oil.

5. The personal cleansing composition of claim 1 comprising from about 2% wt to about 4% wt fragrance oil.

6. The personal cleansing composition of claim 1, wherein the fragrance oil has a boiling point of less than or equal to about 500° C.

7. The personal cleansing composition of claim 1, wherein the fragrance oil has a ClogP of greater than about 0.1.

8. The personal cleansing composition of claim 1, wherein the fatty alcohol comprises $C_8$-$C_{18}$ fatty alcohol.

9. The personal cleansing composition of claim 1, wherein the fatty alcohol comprises lauryl alcohol.

10. The personal cleansing composition of claim 1, wherein the fatty acid comprises $C_8$-$C_{18}$ fatty acid.

11. The personal cleansing composition of claim 1, wherein the fatty acid comprises lauric acid.

12. The personal cleansing composition of claim 1, wherein the salt comprises magnesium or sodium salts of sulfates or chlorides or mixtures of these materials.

13. The personal cleansing composition of claim 1 comprising less than about 5% wt Non-Fragrance Oil.

14. The personal cleansing composition of claim 1 comprising less than about 1% wt Non-Fragrance Oil.

15. The personal cleansing composition of claim 1 comprising no Non-Fragrance Oil.

16. The personal cleansing composition of claim 1 additionally comprising a material selected from the group consisting of cationic polymers, anionic polymers and mixtures thereof.

17. The personal cleansing composition of claim 1 comprising a hydrophilic conditioning agent.

18. The personal cleansing composition of claim 17, wherein the hydrophilic conditioning agent comprises glycerol.

19. The personal cleansing composition of claim 1, wherein the personal cleansing composition is a shampoo or a body wash.

20. A personal cleaning composition consisting essentially of:
   a) a surfactant matrix comprising from about 11.0% wt to 18% wt of a mixture of surfactants comprising:
      i. an anionic surfactant;
      ii. an amphoteric surfactant;
         wherein the ratio of anionic surfactant to amphoteric surfactant is from about 6:1 to about 1:3;
   b) from about 1.5% wt to about 5% wt a fragrance oil;
   c) a material selected from fatty acid, fatty alcohol, salt and mixtures thereof; and
   d) trihydroxystearin;
   wherein upon the addition of the fragrance oil to the surfactant matrix, the personal
   cleaning composition comprises a) a first micellar phase; and b) a second opaque phase which rotates polarized light;
   wherein the personal cleaning composition has a viscosity past the Viscosity Transition Point and an opacity past the Opacity Transition Point; and
   wherein the personal cleaning composition has a lather volume of greater than 150 mL.

21. A personal cleaning composition comprising
   a) a surfactant matrix comprising from about 11.0% wt to 18% wt of a mixture of surfactants comprising:
      i. an anionic surfactant;
      ii. an amphoteric surfactant;
         wherein the ratio of anionic surfactant to amphoteric surfactant is from about 6:1 to about 1:3;
   b) from about 1.5% wt to about 5% wt a fragrance oil;
   c) a material selected from fatty acid, fatty alcohol, salt and mixtures thereof; and trihydroxystearin;
   wherein upon the addition of the fragrance oil to the surfactant matrix, the personal
   cleaning composition comprises a) a first micellar phase; and b) a second opaque phase which rotates polarized light;
   wherein the personal cleaning composition has a viscosity past the Viscosity Transition Point and an opacity past the Opacity Transition Point; and
   with the proviso that the surfactant matrix is free from a hydrophobic silicone phase; and
   wherein the personal cleaning composition has a lather volume of greater than 150 mL.

* * * * *